United States Patent [19]

Yu et al.

[11] Patent Number: 4,592,867
[45] Date of Patent: Jun. 3, 1986

[54] SYNTHESIS METHOD FOR REDUCTANT PRECURSOR

[75] Inventors: Terry T. Yu, Mt. Clemens; Mei-Rong Yen, Troy, both of Mich.

[73] Assignee: Energy Conversion Devices, Inc., Troy, Mich.

[21] Appl. No.: 662,683

[22] Filed: Oct. 19, 1984

[51] Int. Cl.[4] ............... C07C 50/10; C07C 50/16; C07C 50/22; C07C 50/24
[52] U.S. Cl. .................. 260/351.1; 260/396 R
[58] Field of Search .......... 260/396 R, 351.1, 365

[56] References Cited

U.S. PATENT DOCUMENTS

| | | | |
|---|---|---|---|
| 4,164,503 | 8/1979 | Kende et al. | 260/365 |
| 4,229,478 | 10/1980 | Jones et al. | 260/396 R |
| 4,419,368 | 12/1983 | Jones et al. | 260/396 R |
| 4,460,678 | 7/1984 | Yu et al. | 260/396 R |
| 4,532,078 | 7/1985 | Yu et al. | 260/396 R |

FOREIGN PATENT DOCUMENTS

| | | | |
|---|---|---|---|
| 7403 | 2/1980 | European Pat. Off. | 260/365 |
| 3309719 | 9/1984 | Fed. Rep. of Germany | 260/396 R |
| 110581 | 7/1983 | Japan | 260/396 R |
| 88607 | 9/1983 | Japan | 260/396 R |
| 677443 | 9/1949 | United Kingdom | 260/396 R |

OTHER PUBLICATIONS

*Chemical Abstract*, vol. 66, #28720w, 1966, Kerfanto et al., Aminolysis of Halogen Derivatives.

*Primary Examiner*—Glennon H. Hollrah
*Assistant Examiner*—Raymond Covington
*Attorney, Agent, or Firm*—James D. Ryndak

[57] ABSTRACT

A synthesis method is provided for the synthesis of quinone compounds of the formula

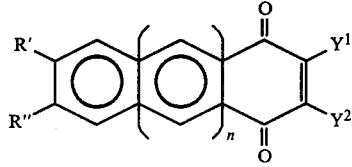

where n is 0–3, $Y^1$ is alkoxy, $Y^2$ is alkoxy, chloro, bromo or hydrogen and $R'$ and $R''$ each and independently are hydrogen, alkyl or phenyl. These compounds are useful as reductant precursors in tellurium imaging compositions.

15 Claims, No Drawings

SYNTHESIS METHOD FOR REDUCTANT PRECURSOR

THE PRIOR ART BACKGROUND

Various methods are known for producing images or duplicates of images. The imaging materials used are, in certain cases, particular organic compounds. Some of these heretofore known methods employ mixtures of inorganic compounds such as silver-halide with one or more particular types of organic compounds as sensitizers.

A new photographic process using tellurium compounds to provide the image is disclosed in U.S. patent application Ser. No. 596,646, filed July 17, 1975 (now U.S. Pat. No. 4,142,896). In accordance with U.S. Pat. No. 4,142,896, an emulsion is formed using certain reducible tellurium compounds in combination with a reductant precursor in a binder or matrix suitable for forming a film-like coating on a substrate. The film prepared therefrom is exposed image-wise to activating energy and is thereafter developed as is known in the art hereinafter described. Heat development is preferred.

Some tellurium compounds described for use in the photographic process of U.S. Pat. No. 4,142,896 may be represented, for example, by the formula

$$R_x\text{—Te—}X_y \quad (1)$$

in which R is an organic radical containing at least one carbonyl group, X is halogen, preferably chlorine, and x is 1, 2 or 3, and $x+y=4$. The organic radical R may be either two independent radicals or may be joined together to form a cyclic compound. Another group of compounds mentioned in U.S. Pat. No. 4,142,896 are organic tellurium compounds which may be considered or characterized as tellurium tetrahalide adducts of ethylenic or acetylenic hydrocarbons. Some of such compounds can be represented by the formulae

$$\begin{array}{c} X \\ | \\ X\text{—R—Te—}R^1\text{—X} \\ | \\ X \end{array} \quad (2)$$

$$(X\text{—R})_n\text{—Te—}X_n \quad (3)$$

wherein R and $R^1$ are each the residue of an ethylenic hydrocarbon and X is a halogen, preferably chlorine.

Another category of photosensitive tellurium compounds which have been found useful are halogenated tellurium compounds, such as compounds of the formula

$$TeCl_nBr_m \quad (4)$$

where n is an integer from 2 to 4, and $n+m=4$. The use of such halogenated tellurium compounds in imaging processes is disclosed in U.S. Pat. No. 4,066,460 to Chang et al.

Still another category of useful tellurium compounds is described in U.S. Pat. No. 4,106,939. These compounds are tellurium tetrahalide adducts of aromatic amines in which nitrogen attached directly or indirectly to the aromatic ring is substituted by alkyls of 1-4 carbon atoms, the adduct being free of diazo groups.

The tellurium compounds such as the foregoing may be employed in conjunction with a reductant-precursor which serves as a sensitizer. The reductant-precursor is a compound which, under the influence of activating energy, will absorb radiation energy and abstract labile hydrogen from an appropriate hydrogen donor to become a strong reducing agent. The strong reducing agent reduces the tellurium compound to a divalent tellurium compound or to elemental tellurium. In either event, a change in optical density occurs which results in an imaging suitable for recording information. In general terms, the foregoing reaction may be represented by the following mechanism:

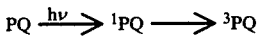
$$PQ \xrightarrow{h\nu} {}^1PQ \longrightarrow {}^3PQ$$

$${}^3PQ + 2RH \longrightarrow PQ.H_2 + R\text{—}R$$

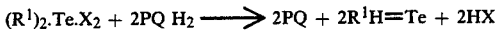
$$(R^1)_2.Te.X_2 + 2PQ\,H_2 \longrightarrow 2PQ + 2R^1H = Te + 2HX$$

wherein PQ is the reductant precursor sensitizing agent; $^1PQ$ is the first excited singlet state thereof; $^3PQ$ is the triplet state thereof; RH is the hydrogen donor; $PQ.H_2$ is the reductant precursor in its reduced state; and $(R^1)_2.Te.X_2$ is the reducible tellurium image-forming compound.

In this connection, it should be noted that the hydrogen donor need not be specifically provided, although a variety of alcohols can be used if desired. In the absence of a specially-provided hydrogen donor, the labile hydrogen can sometimes be abstracted from the organic resins used as binders. In other cases, the sensitizer can be its own hydrogen donor, and this is known to be the case with at least one sensitizer, namely, isopropoxynaphthoquinone.

A modification of the tellurium photographic process is described in Belgian Pat. No. 854,193, wherein certain diols of the formula

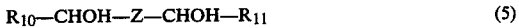
$$R_{10}\text{—CHOH—Z—CHOH—}R_{11} \quad (5)$$

may be employed as the hydrogen donor for use in conjunction with the photosensitizer described above. In the foregoing formula, $R_{10}$ and $R_{11}$ represent hydrogen and various organic substituents. Z may be a direct carbon-carbon linkage between the two hydroxy substituted carbon atoms, or may be any of various linking groups. Reference is made to Belgian Pat. No. 854,193 for a fuller description of the diols referred to. In the Belgian patent, these diols are said to serve as hydrogen donors. Subsequent research has suggested that this is not completely accurate. In fact, a major portion of the diol appears to form a complex with the tellurium compound.

This finding has led to the discovery of diols of the general formula

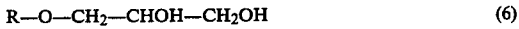
$$R\text{—O—}CH_2\text{—CHOH—}CH_2OH \quad (6)$$

which have improved characteristics when used in tellurium-based photographic films.

The radical R may be a simple aliphatic group (for example, alkyl or alkenyl). Alternatively, the radical R may contain a carbonyl group (for example, an acyl radical). Preferably, however, the radical R is aromatic. Best results are obtained where the aromatic ring is separated from the ether oxygen by one methylene grouping. A more complete description of these diols is contained in U.S. patent application Ser. No. 73,700, filed Sept. 10, 1979, now U.S. Pat. No. 4,281,058, and reference is made thereto for additional descriptions thereof.

Still another modification in the use of tellurium compounds as photosensitive agents involves what is known as a "masked reducing agent." A number of compounds are known, such as phenidone, which will reduce organo-tellurium compounds. The reducing capacity of such compounds may be "masked"—i.e., inhibited—by appropriate substitution. In such cases, if the substituent is one which can be cleaved by the reaction products liberated upon the photo-reduction of the tellurium compound, the masked reducing agent can be used to amplify the photoresponse through the mechanism Light + Sensitizer ⟶ Photoactive Reducing Agent Photoactive Reducing Agent + Tellurium Compound ⟶

Tellurium + By-Products

By-Products + Masked Reducing Agent ⟶

Demasked Reducing Agent

Demasked Reducing Agent + Tellurium Compound ⟶

Tellurium + By-Products

Since the organo-tellurium compounds commonly used release hydrogen halides (particularly hydrogen chlorides) as by-products of the reduction reaction, and the reducing agents, such as phenidone, are amino compounds, the masking agents most effectively employed are compounds which will convert the amino nitrogen into an amide. A typical masked reducing agent thus is the compound

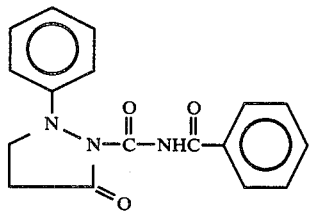
(7)

A more complete description of masked reducing agents may be found in Belgian Pat. No. 863,052 of July 19, 1978, and reference thereto is made for additional descriptions thereof.

As an alternative to the masked reducing agents described in Belgian Pat. No. 863,052, a new class of masked reducing agents may be substituted, represented by the general formulae

(8)

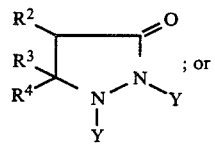
; or
(9)

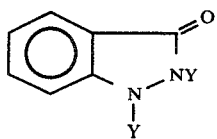
(10)

wherein Y is hydrogen or

said compound containing at least one

group. In the foregoing formulae, $R^1$ may be alkyl, alkanoyl, alkoxycarbonyl, phenyl, benzyl, benzoyl, nitrophenyl, benzylcarbonyl, phenylmethyl, phenylethyl or phenylpropylcarbonyl, or aminocarbonyl. $R^2$, $R^3$ and $R^4$ each, and independently, may be hydrogen, alkyl or phenyl and amino. $R^4$ may be phenyl, nitrophenyl, halophenyl, alkyl, mono-, di- or tri-haloalkyl, benzoyl, alkylphenyl, or alkylcyanophenyl. The masking group may be substituted at either one or both of the amino hydrogen sites of the reducing agent. The alkyl groups referred to above may contain up to seven carbon atoms. Such compounds are conveniently accessible through reaction of the parent hydrazine or pyrazoline with an isocyanate of the formula

(11)

A more complete description of these masked reducing agents is found in U.S. patent application Ser. No. 277,720, filed June 26, 1981, and reference thereto is made for additional descriptions thereof.

In practice, the foregoing ingredients, i.e., a tellurium derivative, a reductant precursor sensitizer, and additional ingredients such as the glycol and masked reducing agent, are combined in a suitable matrix to form an emulsion which may be spread into a film on an appropriate carrier or substrate. A latent image in the film is formed by exposure to imaging energy, for example, a light image.

After formation of the latent image, a visible image is developed by heating the exposed film as described in U.S. Pat. No. 4,142,896.

The speed or light sensitivity of the film is determined by the amount of energy necessary to produce an image. For many applications it is desirable to have an imaging film that is relatively fast, and in addition, has a low optical density relative to the optical density of the image formed by the film. It is also desirable for the film to be sensitive to light in the visible spectrum facilitating use of the film in many practical applications. The organo-tellurium imaging system previously described generally did not possess the characteristics of sensitivity to visible light while at the same time having good speed, such as less than about 30,000 ergs of imaging energy per square centimeter to achieve an optical density of one greater than fog.

U.S. patent application Ser. No. 392,586, filed June 28, 1982, entitled "Tellurium Imaging Composition Including Improved Reductant Precursor and Method," now U.S. Pat. No. 4,460,678, hereby incorporated by reference, discloses improved tellurium imaging compositions. The improvement results from certain types of reductant precursors which are quinones. The quinones disclosed therein include those of the general formulae:

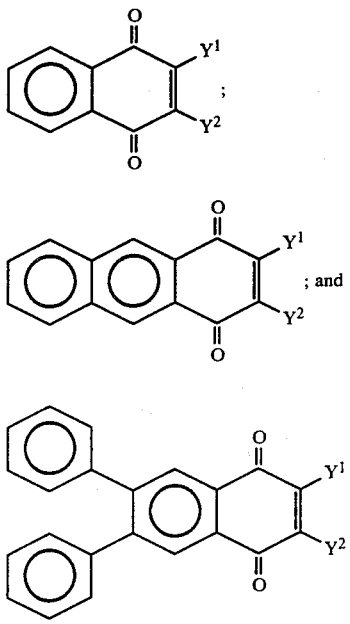

(12)

(13)

(14)

wherein $Y^1$ is alkoxy, generally having less than 6 carbon atoms, (methoxy, ethoxy, propoxy, butoxy, pentoxy, etc.), $Y^2$ is alkoxy, generally having less than 6 carbon atoms (methoxy, ethoxy, propoxy, butoxy, pentoxy, etc.), hydrogen or chloro. Generally, best results are obtained in tellurium imaging film when $Y^1$ has greater than one carbon atom. Use of the quinone compounds (12), (13) or (14) can result in unexpected improvements in spectral sensitivity and/or speed of tellurium imaging film.

While U.S. patent application Ser. No. 392,586 discloses methods for making quinone compounds (12)–(14), it would be desirable to have an improved synthesis method for producing these compounds.

SUMMARY OF THE INVENTION

In accordance with the invention, improved methods of synthesis are provided for making compounds of the general formula:

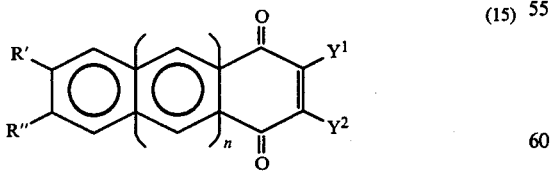

(15)

where "n" is 0–3, $Y^1$ is alkoxy, $Y^2$ is alkoxy, chloro, bromo or hydrogen and R′ and R″ each and independently are hydrogen, alkyl or phenyl. Generally, the alkoxy of $Y^1$ and $Y^2$ will have less than six carbon atoms (methoxy, ethoxy, propoxy, butoxy, pentoxy, etc.). Thus, for example, compounds which can be synthesized in accordance with the invention include those of the following formulae:

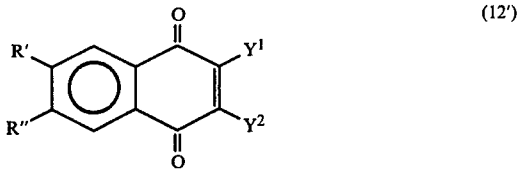

(12′)

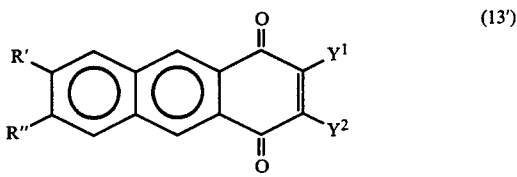

(13′)

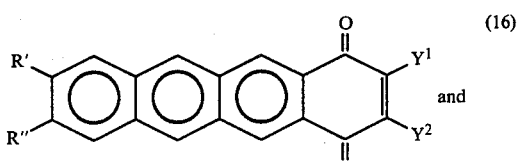

(16)

and

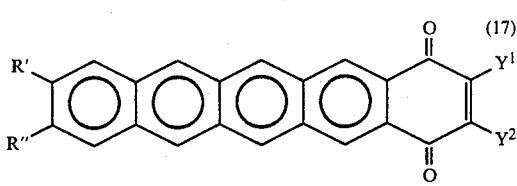

(17)

In accordance with the invention, a compound of the general formula

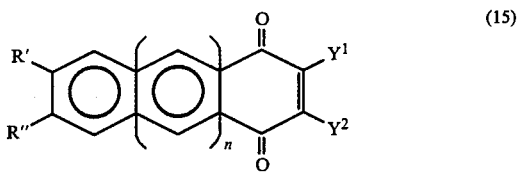

(15)

is synthesized as follows. A 2-alkoxyhydroquinone having its alkoxy group corresponding to the alkoxy of $Y^1$, or $Y^2$, if $Y^2$ is to be alkoxy, is reacted with lead tetraacetate, lead dioxide ($PbO_2$) or a similar oxidizing agent, to form the corresponding 2-alkoxy-1,4-benzoquinone.

Thereafter, the corresponding 2-alkoxy-1,4-benzoquinone is reacted with the reaction mixture of potassium iodide and:

(1) with a compound of the formula:

(18)

if it is desired to form a naphthoquinone, to form the corresponding 2-alkoxy-1, 4-napthoquinone;

(2) with a compound of the formula:

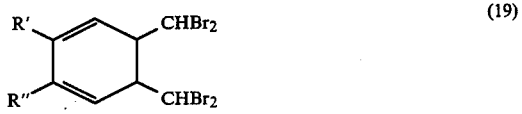

(19)

if it is desired to form an anthraquinone, to form the corresponding 2-alkoxy-1, 4-anthraquinone;

(3) with a compound of the formula:

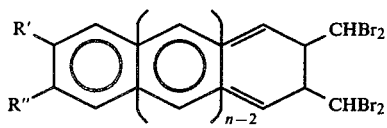
(20)

where n is a number corresponding to n of compound (15) where n is two or three, if it is desired to form a compound of the formula:

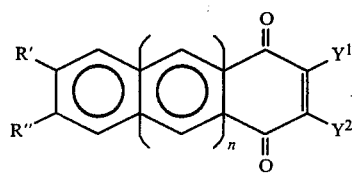
(15)

where n is 2 or 3.

In each of the foregoing reactions, the compound 18, 19 or 20 can be reacted with potassium iodide prior to reaction with the 2-alkoxy-1,4-benzoquinone. Generally a better yield is provided if one of the compounds 18, 19 or 20 is reacted with potassium iodide prior to addition of the 2-alkoxy-1,4-benzoquinone, than if the reactants are added concurrently.

The reaction of the 2-alkoxy-1, 4-benzoquinone with an appropriate compound (18, 19 or 20) results in the compound of the general formula

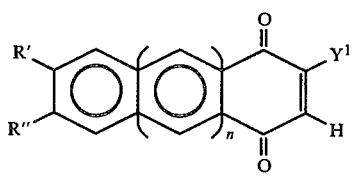
(21)

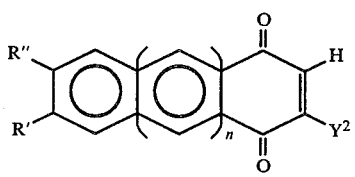
(22)

where $Y^1$ in compound (21) and $Y^2$ in compound (22) is the alkoxy of the starting compound 2-alkoxyhydroquinone. If the desired final compound has hydrogen in the $Y^1$ or $Y^2$ position, then no further steps are necessary. If $Y^1$ or $Y^2$ respectively, in compounds (22) and (21) is to be chloro or bromo, then the following additional steps are taken. The compound (21) or (22) is reacted with chlorine ($Cl_2$) or bromine ($BR_2$) to substitute Cl— or Br—, respectively, for H— in the $Y^1$ or $Y^2$ position. Generally, this reaction is carried out in a solvent, such as carbon tetrachloride or methylene chloride:

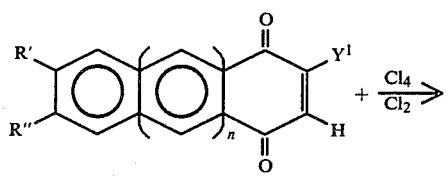
(23)

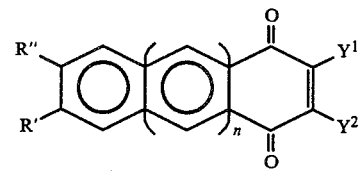

If the $Y^1$ or $Y^2$ position of compounds (21) or (22), respectively, is to be alkoxy, then after substitution of H with Cl, or Br, the compound, such as (23) is reacted with an alkali metal salt of the desired alkoxy, e.g. X—OR (24) where X is the alkali metal, such as potassium, sodium, or lithium, and OR represents the desired alkoxy group.

This reaction can take place in a solvent (such as an alcohol R—OH (25)) in which the R group of compound (25) corresponds to the R group of compound (24) or benzyl. Preferably, the solvent is the corresponding alcohol. For example:

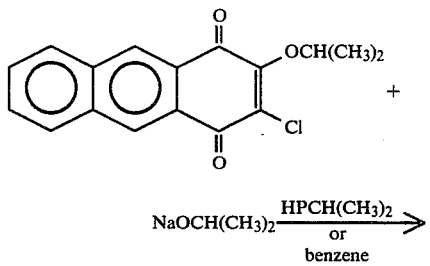

$$NaOCH(CH_3)_2 \xrightarrow[\text{benzene}]{\text{HPCH}(CH_3)_2 \text{ or}}$$

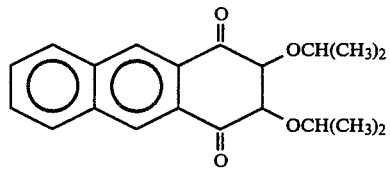

DETAILED DESCRIPTION

Representative quinone compounds which can be synthesized in accordance with the invention are, for example: 3-chloro-2-isopropoxy-1, 4-naphthoquinone; 3-chloro-2-isopropoxy-6, 7-diphenyl-1, 4-naphthoquinone; 3-chloro-2-isopropoxy-1, 4-anthraquinone; 3-chloro-2-(3'-pentoxy)-1, 4-naphthoquinone; 3-chloro-2-(2'-butoxy)-1, 4-naphthoquinone; 3-chloro-2-(3',3'-dimethyl-2'-butoxy)-1, 4-naphthoquinone, 2,3-diisopropoxy-1, 4-naphthoquinone; 3-chloro-2-methoxy-1, 4-naphthoquinone; 2,3-dimethoxy-1,4-naphthoquinone; 3-chloro-2-(t-butoxy)-1,4-naphthoquinone; 3-chloro-2-ethoxyl-4-naphthoquinone; 3-chloro-2-(n-butoxy-)-1,4-naphthoquinone; 3-chloro-2-(2'-methylpropoxy)-1,4-naphthoquinone; 2-isopropoxy-1,4-anthraquinone; 2,3 diisopropoxy-1,4-anthraquinone; 3-chloro-2-(2'-butoxy)-1,4-anthraquinone; 2,3-dimethoxy-1,4-anthraquinone; 3-chloro-2-(t-butoxy)-1,4-anthraquinone; 3- chloro-2-ethoxy-1,4-anthraquinone; and 3-chloro-2-(n-butoxy)-1,4-anthraquinone.

The synthesis method of the present invention is preferably used to make desired anthraquinones.

The reductant precursors, when incorporated into the organo-tellurium imaging system can result in imaging film having increased sensitivity to visible light at relatively high speed compared to other reductant precursors.

The synthesis method in accordance with the present invention results in relatively high yields of the reductant precursor quinone compound. For example, significantly higher yields, on the order of about five to ten times, of the reductant precursor anthraquinone compounds of the type described herein are obtained compared to the synthesis methods disclosed in U.S. patent application Ser. No. 392,586.

The reductant precursor quinone compounds are synthesized with a 2-alkoxyhydroquinone as a starting material. Synthesis methods for making such alkoxyhydroquinone compounds are well known to those skilled in the art. For example, hydroquinone can be synthesized from aniline by oxidizing it to form quinone by manganese dioxide and then reducing quinone to form hydroquinone. Hydroquinone can then be substituted at the 2-position by reaction with sodium alkoxide.

Compounds 18–19 and methods of making them are known to those skilled in the art, and therefore, no description of such synthesis is provided.

While not wishing to be bound by theory, it is believed that reaction of any one of compounds 18, 19 or 20 with potassium iodide in the presence of heat forms a respective intermediate compound:

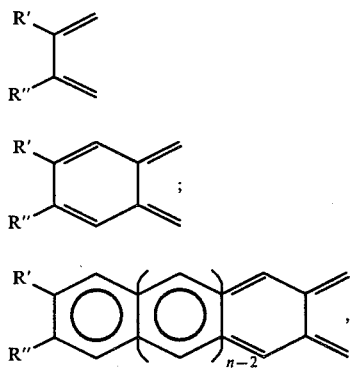

(18a)

(19a)

(20a)

that reacts with the desired 2-alkoxyhydroquinone to provide the desired compound. Generally, the desired 2-alkoxyhydroquinone will be added after the potassium iodide is dissolved in the solvent. However, the three components can be added together simultaneously, although better yields are generally obtained where the 2-alkoxyhydroquinone is not added until the potassium iodide is dissolved in the solvent.

Other compounds and reagents previously referred to are known to those skilled in the art and are easily obtainable and/or synthesized. These compounds and reagents include lead tetraacetate (Pb(oAc)$_4$), potassium iodide (KI), alkali metal salts of alcohols (such as Na—O—R, where R is alkyl), and other miscellaneous reagents as disclosed herein.

The invention is further illustrated by the following examples:

EXAMPLE 1

Preparation of 2-methoxy-1,4-benzoquinone (1)

30 g of acetic acid prewashed lead tetraacetate was added to a suspension of 10 g of 2-methoxyhydroquinone in 200 ml of benzene. The reaction mixture was stirred at room temperature for 2 to 3 hours. The white lead acetate, Pd(oAc)$_2$, a by-product, formed during the reaction was removed by filtration. After removal of solvent under reduced pressure, 10 g of crude 2-methoxy-1,4-benzoquinone was obtained. The crude product was used in the next reaction.

EXAMPLE 2

Preparation of 2-methoxy-1,4-anthraquinone (2) (MAQ)

16 g of, α, α, α', α', -tetrabromo-o-xylene, 44 g of potassium iodide and 10 g crude 2-methoxy-1,4-benzoquinone were stirred in 160 ml of N,N-dimethylformamide at 70° C. overnight. After the reaction was complete, no bromide was left as determined by thin layer chromotography and the reaction mixture was poured into 1200 ml of H$_2$O. 10%aq Na$_2$S$_2$O$_5$ solution was added to decolorize the solution. The precipitate formed in the aqueous solution was collected and dried. Continuous extraction of the dark precipitate using benzene as a solvent yielded a dark colored solution. The solution was then washed with 2.5% NaOH, H$_2$O, dried and concentrated. 7 g of crude product was obtained. Recrystallization from methanol yielded 5 g of pure yellow powder of MAQ.

EXAMPLE 3

Preparation of chloro-methoxy-1,4-anthraquinone (3) (CMAQ)

4 g of chlorine was bubbled into 100 ml of carbon tetrachloride, CCl$_4$. The chlorine solution was then added to a suspension of 4 g of MAQ 1 n 100 ml of CCl$_4$. After the addition, the reaction mixture was refluxed until it became a clear solution (approximately 4–5 hours). Removal of the solvent yielded a crude oil. 4 g of pure yellow crystals of CMAQ was obtained after recrystallization from methanol.

EXAMPLE 4

Preparation of 2,3-diisopropoxy-1,4-anthraquinone (4) (DIPAQ)

1 g of sodium and 200 ml of isopropanol were refluxed to prepare the alkoxide, sodium isopropoxide. The alkoxide solution was then added dropwise to a previously cooled suspension of 3 g of CMAQ in 100 ml of isopropanol at 0°–5° C. The reaction mixture was brought to room temperature and stirred for 30 minutes. After the completion of the reaction, 300 ml of benzene was added to the mixture. The mixture was then washed with 6N HCl (to neutralize the mixture), 2.5% NaOH (to remove impurities), water, dried and concentrated. Recrystallization of the crude concentrate in isopropanol yielded 2.5 g of pure yellow crystals of DIPAQ.

EXAMPLE 5

Preparation of 2-isopropoxy-1,4-anthraquinone (5) (IPAQ)

17 ml of cold borontrifluoride etherate was added to a suspension of 7 g of 2-methoxy-1,4-anthraquinone in 120 ml of isopropanol. The reaction was carried at 70°–80° C. overnight. After partially concentrated, the reaction mixture was left at room temperature and the crude product was obtained as dark brown precipitate. Recrystallization from isopropanol yielded 5 g of pure yellow needles of IPAQ.

EXAMPLE 6

Preparation of chloro-isopropoxy-1,4-anthraquinone (6) (CIPAQ)

1 g of chlorine was bubbled into a solution of 1 g of 2-isopropoxy-1,4-anthraquinone (IPAQ) in 50 ml of methylene chloride at room temperature. The reaction completed within 30 minutes. Removal of the solvent yielded gum-like crude product. After recrystallization from isopropanol, 1.2 g of pure yellow crystals of CIPAQ was obtained.

NOTE: All reactions in Examples 1 through 6 were carried out under red light.

While the invention has been described with respect to certain embodiments, it is to be understood that numerous changes, modifications and rearrangements will be apparent to one skilled in the art and it is intended to cover all such changes, modifications and rearrangements which fall within the scope of the appended claims.

We claim:

1. A method of synthesizing an anthraquinone of the formula:

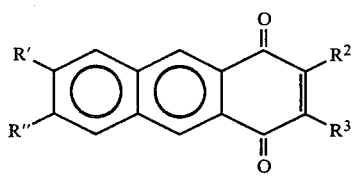

(15)

where $R^2$ is lower alkoxy, $R^3$ is lower alkoxy, chloro, bromo or hydrogen, $R'$ and $R''$ each and independently are hydrogen, lower alkyl or phenyl, comprising:

(a) reacting the compound

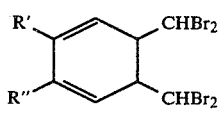

with potassium iodide;

(b) reacting a 2-alkoxy-1,4-benzoquinone where the lower alkoxy corresponds to $R^2$ with the reaction mixture from (a) to form the corresponding 2-alkoxy-1,4-anthraquinone;

(c) thereafter, if $R^3$ is lower alkoxy, chloro or bromo reacting the corresponding 2-alkoxy-1,4-anthraquinone with a halogen selected from the group consisting of chlorine and bromine to form 2-alkoxy,3-halo-1,4-anthraquinone; and (d) thereafter, if $R^3$ is lower alkoxy, reacting the 2-alkoxy,3-halo-1,4-anthraquinone with X—O $R^4$, where X is an element selected from the group consisting of lithium sodium and potassium and —O $R^4$ corresponds to the lower alkoxy represented by $R^3$, to form the anthraquinone:

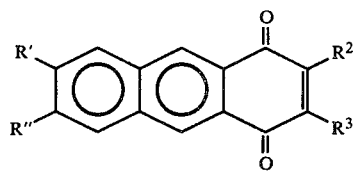

where $R^2$ is lower alkoxy and $R^3$ is lower alkoxy corresponding to —O $R^4$.

2. The method of claim 1 wherein $R^2$ is selected from the group consisting of methoxy, ethoxy, butoxy, propoxy, and pentoxy and $R^3$ is selected from the group consisting of methoxy, ethoxy, butoxy, propoxy and pentoxy.

3. The method of claim 1 wherein $R^2$ is isopropoxy and $R^3$ is chloro.

4. The method of claim 1 wherein $R^2$ is isopropoxy and $R^3$ is isopropoxy.

5. The method of claim 1 wherein the reactants of steps (a) and (b) are added concurrently.

6. A method of synthesizing an naphthoquinone of the formula:

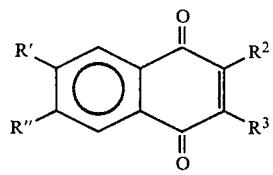

where $R^2$ is lower alkoxy, $R^3$ is lower alkoxy, chloro, bromo or hydrogen comprising:

(a) reacting the compound

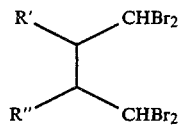

with potassium iodide;

(b) reacting a 2-alkoxy-1,4-benzoquinone where the lower alkoxy corresponds to $R^2$ with the reaction mixture from (a) to form the corresponding 2-alkoxy-1,4-naphthoquinone;

(c) thereafter, if $R^3$ is lower alkoxy, chloro or bromo, reacting the corresponding 2-alkoxy-1,4-naphthoquinone with a halogen selected from the group consisting of chlorine and bromine to form 2-alkoxy,3-halo-1,4-naphthoquinone; and (d) thereafter, if $R^3$ is lower alkoxy, reacting the 2-alkoxy,3-halo-1,4-naphthoquinone with X—O $R^4$, where X is an element selected from the group consisting of lithium, sodium and potassium and —O $R^4$ corresponds to the lower alkoxy represented by $R^3$, to form the naphthoquinone:

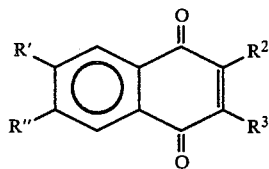

(12)

where $R^2$ is lower alkoxy and $R^3$ is lower alkoxy corresponding to $-OR^4$.

7. The method of claim 6 wherein $R^2$ is selected from the group consisting of methoxy, ethoxy, butoxy, propoxy, and pentoxy and $R^3$ is selected from the group consisting of methoxy, ethoxy, butoxy, propoxy and pentoxy.

8. The method of claim 6 wherein $R^2$ is isopropoxy and $R^3$ is chloro.

9. The method of claim 6 wherein $R^2$ is isopropoxy and $R^3$ is isopropoxy.

10. The method of claim 6 wherein the reactants of steps (a) and (b) are added concurrently.

11. A method of synthesizing a compound of the formula:

(16)

where $R^2$ is lower alkoxy, $R^3$ is lower alkoxy, chloro, bromo or hydrogen and R' and R'' each and independently are hydrogen, lower alkyl comprising:

(a) reacting the compound with potassium iodide;

(b) reacting a 2-alkoxy-1,4-benzoquinone where the lower alkoxy corresponds to $R^2$ with the reaction mixture from (a) to form (c) thereafter, if $R^3$ is lower alkoxy, chloro or bromo, reacting with a halogen selected from the group consisting of chlorine and bromine to form:

(d) thereafter, if $R^3$ is lower alkoxy, reacting with $X-OR^4$, where X is an element selected from the group consisting of lithium, sodium and potassium and $-OR^4$ corresponds to the lower alkoxy represented by $R^3$, to form the compound:

where $R^2$ is lower alkoxy and $R^3$ is lower alkoxy corresponding to $-OR^4$.

12. The method of claim 1 wherein $R^2$ is selected from the group consisting of methoxy, ethoxy, butoxy, propoxy, and pentoxy and $R^3$ is selected from the group consisting of methoxy, ethoxy, butoxy, propoxy and pentoxy.

13. The method of claim 11 wherein $R^2$ is isopropoxy and $R^3$ is chloro.

14. The method of claim 11 wherein $R^2$ is isopropoxy and $R^3$ is isopropoxy.

15. The method of claim 11 wherein the reactants of steps (a) and (b) are added concurrently.

* * * * *